United States Patent
Durnell et al.

(10) Patent No.: US 8,908,917 B2
(45) Date of Patent: Dec. 9, 2014

(54) EYE TRACKING APPARATUS INCLUDING INDICATION OF EYE DIRECTION

(75) Inventors: Laurence Durnell, Alton (GB); Donald Nigel Jarrett, Bristol (GB)

(73) Assignee: Qinetiq Limited, Hampshire (GB)

( * ) Notice: Subject to any disclaimer, the term of this patent is extended or adjusted under 35 U.S.C. 154(b) by 155 days.

(21) Appl. No.: 13/511,306

(22) PCT Filed: Nov. 25, 2010

(86) PCT No.: PCT/GB2010/002165
§ 371 (c)(1),
(2), (4) Date: May 22, 2012

(87) PCT Pub. No.: WO2011/064534
PCT Pub. Date: Jun. 3, 2011

(65) Prior Publication Data
US 2012/0230547 A1  Sep. 13, 2012

(30) Foreign Application Priority Data

Nov. 27, 2009 (GB) .................................. 0920809.1

(51) Int. Cl.
| | | |
|---|---|---|
| G06K 9/00 | (2006.01) | |
| A61B 3/113 | (2006.01) | |
| G06F 3/01 | (2006.01) | |

(52) U.S. Cl.
CPC ................ *A61B 3/113* (2013.01); *G06F 3/013* (2013.01)
USPC ........................................................ 382/103

(58) Field of Classification Search
None
See application file for complete search history.

(56) References Cited

U.S. PATENT DOCUMENTS

| | | | |
|---|---|---|---|
| 4,836,670 A | 6/1989 | Hutchinson | |
| 6,433,760 B1 | 8/2002 | Vaissie et al. | |
| 6,659,611 B2 * | 12/2003 | Amir et al. | 351/210 |
| 7,384,399 B2 | 6/2008 | Ghajar | |
| 7,391,887 B2 * | 6/2008 | Durnell | 382/117 |
| 7,401,920 B1 * | 7/2008 | Kranz et al. | 351/210 |
| 7,522,344 B1 | 4/2009 | Curatu et al. | |
| 2003/0123027 A1 * | 7/2003 | Amir et al. | 351/209 |
| 2004/0196433 A1 * | 10/2004 | Durnell | 351/209 |
| 2006/0093998 A1 | 5/2006 | Vertegaal | |
| 2006/0110008 A1 | 5/2006 | Vertegaal et al. | |
| 2006/0256083 A1 | 11/2006 | Rosenberg | |
| 2006/0270945 A1 * | 11/2006 | Ghajar | 600/558 |
| 2012/0230547 A1 * | 9/2012 | Durnell et al. | 382/103 |

FOREIGN PATENT DOCUMENTS

| | | |
|---|---|---|
| EP | 0 733 338 A1 | 9/1996 |
| WO | WO 03/017203 A1 | 2/2003 |

OTHER PUBLICATIONS

International Search Report issued in International Application No. PCT/GB2010/002165 dated Mar. 15, 2011.
Written Opinion issued in International Application No. PCT/GB2010/002165 dated Mar. 15, 2011.
Search Report issued in British Application No. 0920809.1 dated Mar. 11, 2010.

* cited by examiner

*Primary Examiner* — Tahmina Ansari
(74) *Attorney, Agent, or Firm* — Oliff PLC

(57) ABSTRACT

An eye tracking apparatus and method of eye monitoring, comprising a target display adapted to project a moveable image of a target into a user's field of vision, an illumination source adapted to project a reference point onto a user's eye, a sensor adapted to monitor a user's eye, and a processor adapted to determine the position of a feature of a user's eye relative to the reference point, wherein the apparatus is arranged such that said determined position provides a direct indication of eye direction relative to the target direction.

21 Claims, 2 Drawing Sheets

EYE TRACKING APPARATUS INCLUDING INDICATION OF EYE DIRECTION

The present invention relates an eye tracking apparatus and to a method of monitoring the movement of a user's eyes. Without limitation, the invention relates specifically to a portable eye tracking apparatus suitable for medical applications such as assessment of neurological conditions and mild traumatic brain injury (mTBI).

Eye tracking apparatuses are used in medical and research establishments for monitoring the physiological and neurological state of subjects. For example U.S. Pat. No. 7,384,399 describes a system and method for testing a subject for cognitive impairment. However, conventional eye tracking apparatuses and medical equipment incorporating the same are traditionally complex in construction and operation. Conventional eye tracking apparatus incorporates sophisticated display and imaging components making them expensive. Such conventional eye tracking apparatus also requires calibration prior to use and can only be operated by a skilled operator or clinician.

US 2003/0123027A describes an alternative system for eye gaze tracking which does not require active calibration. Specifically, the system of US 2003/0123027A determines the user's point of regard by imaging a test pattern of reference points reflected from the user's cornea. The user's point of regard is calculated indirectly by mapping or mathematically relating the reflected test pattern image to the actual test pattern in real space. Whilst active calibration is obviated, the system of US 2003/0123027A requires the mapping relationship between an image coordinate system and a reference coordinate system to be defined prior to use.

It is an object of the invention to provide an eye tracking apparatus which mitigates at least one disadvantage of conventional devices.

According to a first aspect of the present invention, there is now proposed an eye tracking apparatus comprising a target display adapted to project a moveable image of a target into a user's field of vision, an illumination source adapted to project a reference point onto a user's eye, a sensor adapted to monitor a user's eye, and a processor adapted to determine the position of a feature of a user's eye relative to the reference point, wherein the apparatus is arranged such that said determined position provides a direct indication of eye direction relative to the target direction.

The eye tracking apparatus provides the advantage that the information gathered at the sensor concerning the relative positions of the reference point and the user's eye is by itself sufficient to determine the user's eye direction relative to the target, and inherently contains information concerning the target direction in the user's field of view because of the arrangement of the system. No further information is needed, as opposed to an indirect system where additional reference to a target direction is typically required, e.g. via a calibration step or measurement. The elimination of the calibration process offers potential benefits in terms of increasing the accuracy of eye tracking apparatuses and enabling eye tracking apparatuses to be used by non-specialist operators.

Conventional eye tracking apparatuses typically require calibration prior to use, for example in order determine the absolute position of a user's point of regard in a real or virtual scene. Such calibration usually comprises a process in which the user is asked to fixate their gaze on a point within the scene having a known location therein and simultaneously measuring the position of features of the user's eye using an imaging sensor. The calibration process typically requires a plurality of measurements be taken at a series of calibration points. The user's point of regard in the scene can subsequently be determined from a measurement of the positions of features of the user's eye in an image thereof from the sensor. Alternatively or additionally, a comparison with the location of a visual target then needs to be made, with the target location and user's point of regard in compatible measurement space.

However, the abovementioned calibration process is time-consuming and must normally be conducted by a trained and experienced operator in order to provide reliable eye tracking. The requirement for a trained and experienced operator has hitherto restricted the application of eye tracking apparatuses to medical and research laboratories. This is particularly true in the case of eye tracking apparatuses used for neurological assessments, for example for measuring a subject's cognition, and for assessing mild traumatic brain injuries (mTBI).

The calibration process also accounts for the largest contribution towards inaccuracies in conventional eye tracking apparatuses.

Hence, the elimination of the calibration process offers potential benefits in terms of increasing the accuracy of eye tracking apparatuses and enabling eye tracking apparatuses to be used by non-specialist operators.

Embodiments of the present invention obviate calibration of the eye tracking apparatus through an advantageous arrangement of the target display and the eye sensor within the eye tracking apparatus, such that the sensor images the user's eye along the target direction, which is to say the optical path along which the target is projected into the user's field of view. The angular error of the eye line-of-sight from the direction of the moveable target may then be determined directly by imaging the eye. Where the direction of illumination is also coincident with the target direction, a direct determination of eye direction relative to the target and hence eye-target error is obtained by measuring a distance between the reference point on the user's eye and a physical feature of the user's eye.

In a preferred embodiment, the target display is adapted to project the moveable image along a projection path, the illumination source is adapted to project the reference point along an illumination path, the sensor is adapted to monitor the user's eye along an imaging path, and wherein at least a portion of the projection path, the illumination path and the imaging path are arranged to be substantially coaxial.

It will be understood that the projection path, the illumination path and the imaging path are preferably arranged to be substantially coaxial as they enter the user's field of view. Furthermore it should be clear to the skilled person that said paths may diverge from a common optical path where said paths emanate from the target display and the illumination source and where the imaging path enters the sensor.

In a preferred embodiment, the target and illumination source are effectively coincident, and in certain embodiments the target display and the illumination source may be one and the same.

In embodiments where the target traces a moving path, the apparatus is preferably adapted so that the imaging path of the senor is maintained in alignment along the target direction. That is, the imaging path is coupled to the target projection path.

Preferably therefore, the eye tracking apparatus is arranged to scan the illumination path, the projection path and the imaging path in synchronisation within the user's field of vision. Scanning or tracing is advantageously achieved by a mechanical moving element, such as a rotating prism, mirror or other optical element. In such embodiments the projection path, the illumination path and the imaging path should preferably follow a common optical path through said optical element.

In a preferred embodiment, the sensor is configured to monitor the position of the reference point with respect to a physical feature of the user's eye using an imaging sensor. Without limitation, the sensor may be a photosensitive device (PSD) or an imaging sensor adapted to image the user's eye. Conveniently, the processor is adapted to determining a distance between the position of the reference point and a physical feature of the user's eye.

This is advantageous because the distance between the reference point and the eye feature gives a direct indication of eye-target error due to the coaxial arrangement of reference illumination axis, target projection axis and imaging axis.

Advantageously, the processor is adapted to convert the determined distance into a measurement of an angle between the target direction and the user's eye direction.

The feature of the user's eye desirably comprises at least one of the user's pupil and the user's iris.

For example, the feature of the user's eye may comprise the outer circumference of the pupil or iris of the user's eye. Alternatively, the feature of the user's eye may comprise the centre of the pupil, determined for example from the outer circumference thereof. Similarly, the feature of the user's eye may comprise the centre of the iris, determined for example from the outer circumference thereof.

In a preferred embodiment, the indication of eye direction relative to the target is obtainable by monitoring the concentricity of the reference point and the pupil of the user's eye.

In one embodiment, the eye tracking apparatus is adapted to scan the image of the target in the user's field of vision with a substantially constant angular velocity. This enables the eye tracking apparatus to measure the ability of the user's eye pursue a smoothly moving target image.

Alternatively, the eye tracking apparatus is adapted to scan the image of the target in the user's field of vision with a varying angular velocity.

Preferably, the eye tracking apparatus is adapted to scan the image of the target in the user's field of vision along a controlled path that includes at least one of a point, a line, an arc, a circle, and an ellipse.

The image of the target may be scanned in the user's field of vision using an optical element moveable by at least one of a micro-electromechanical actuator, a motor, a piezo micro-positioner, a galvanometer and a manually operable lever.

In another preferred embodiment, the eye tracking apparatus comprises a modulator adapted to temporally vary at least one of the brightness, the hue, the shape and the form of the image of the target. This enables the eye tracking apparatus to move a changeable target image in a discontinuous scan in order to assess the user's anticipatory response. This is beneficial in that a wider range of cognitive functions can be assessed using the apparatus.

According to a second aspect, there is proposed a method of eye monitoring in which a moveable image of a target is projected into a user's field of vision, and an image of the user's eye is formed on an image sensor, said method comprising: projecting a reference point onto the user's eye, arranging for the selected reference point to provide, in the image, an indication of the position of the target on the user's eye, and analysing the image to determine the position of a feature of the user's eye with respect to the reference point.

Preferably, the method comprises analysing the position of the user's eye relative to the reference point in the image to measure eye tracking of said moving target.

The reference point may projected onto the user's eye by illuminating the eye so as to produce a spot corneal reflex as said reference point.

The method may further comprise projecting the moveable target and the illumination generating the reference point along a common projection path and monitoring the user's eye along an imaging path, wherein at least a portion of said imaging path is substantially coaxial with said common projection path.

It will be understood that the projection path, the illumination path and the imaging path are arranged to be substantially coaxial as they enter the user's field of view. Furthermore it should be clear to the skilled person said paths may diverge from a common optical path where said paths emanate from the target display and the illumination source and where the imaging path enters the sensor.

Preferably, the method comprises the step of scanning the common projection path and the imaging path in synchronisation within the user's field of vision.

Conveniently, the method comprises the step of analysing the image to determine a distance between the feature of the user's eye and the position of the reference point. This is advantageous because the distance between the reference point and the eye feature gives a direct indication of eye-target error due to the coaxial arrangement of reference illumination axis, target projection axis and imaging monitoring axis.

In a preferred embodiment, the method comprises the step of converting the determined distance into a measurement of an angle between the target direction and the user's eye direction.

Conveniently, the feature of the user's eye comprises at least one of the user's pupil and the user's iris.

As explained above, the features of the user's eye may comprise the outer circumference of the pupil or iris of the user's eye. Alternatively, the feature of the user's eye may comprise the centre of pupil, determined for example from the outer circumference thereof. Similarly, the feature of the user's eye may comprise the centre of the iris, determined for example from the outer circumference thereof.

In a preferred embodiment, the indication of the user's eye direction relative to the target is obtainable my monitoring the concentricity of the reference point and the pupil of the user's eye.

In a preferred embodiment, the method comprises the step of scanning the image of the target in the user's field of vision with a substantially constant angular velocity. This enables the eye tracking apparatus to measure the ability of the user's eye pursue a smoothly moving target image.

Alternatively, the method comprises the step of scanning the image of the target in the user's field of vision with a varying angular velocity.

The method may comprise scanning the image of the target in the user's field of vision along a controlled path that includes at least one of a point, a line, an arc, a circle, and an ellipse.

Preferably, the method comprises the step of moving the image of the target in the user's field of vision using an optical element moveable by at least one of a micro-electromechanical actuator, a motor, a piezo micro-positioner, a galvanometer, and a manually operable lever.

The method may also comprise the step of temporally varying at least one of the brightness, the hue, the shape and the form of the image of the target. This enables the method eye monitoring to move a changeable target image in a discontinuous scan in which case the method may also comprise the step of assessing the user' anticipatory response. This is beneficial in that a wider range of cognitive functions can be assessed using the present method.

The invention extends to methods, apparatus and/or use substantially as herein described with reference to the accompanying drawings.

Any feature in one aspect of the invention may be applied to other aspects of the invention, in any appropriate combination. In particular, method aspects may be applied to apparatus aspects, and vice versa.

Preferred features of the present invention will now be described, purely by way of example, with reference to the accompanying drawings, in which:

BRIEF DESCRIPTION OF THE DRAWINGS

FIG. 2a illustrates the image of the user's eye when viewing a high target; FIG. 2b illustrates the image of the user's eye when viewing a target arranged to one side of the user's eye; FIG. 2c illustrates the image of the user's eye when viewing a low target; and FIG. 2d illustrates the image of the user's eye when viewing a target arranged to the other side of the user's eye.

Referring now to the drawings wherein like reference numerals identify corresponding or similar elements throughout the several views, FIG. 1 shows an eye tracking apparatus 2 comprising a target display 4 configured to project an image of a target into the field of vision of a user 6. The target display in the embodiment of FIG. 1 comprises a light emitting diode (LED), however alternatives include a liquid crystal display, a lamp or any display capable of acting as a small, source and emitting electromagnetic radiation having a wavelength in the visible spectrum. A lens 8 receives the electromagnetic radiation emitted from the target display 4 and projects said electromagnetic radiation along a projection path 10 into the user's eye 12 via a semi-reflective mirror 14 and a small angle wedge prism 16. In use, the display 4 appears as a distant target in the user's field of vision. The wedge prism 16 is rotatable about the projection axis 10 by a prism rotation mechanism 18. In the embodiment shown in FIG. 1, the prism rotation mechanism 18 comprises a motor having a shaft mounted pinion arranged in mechanical communication with a gear disposed around the periphery of the wedge prism 16.

Figure 1:
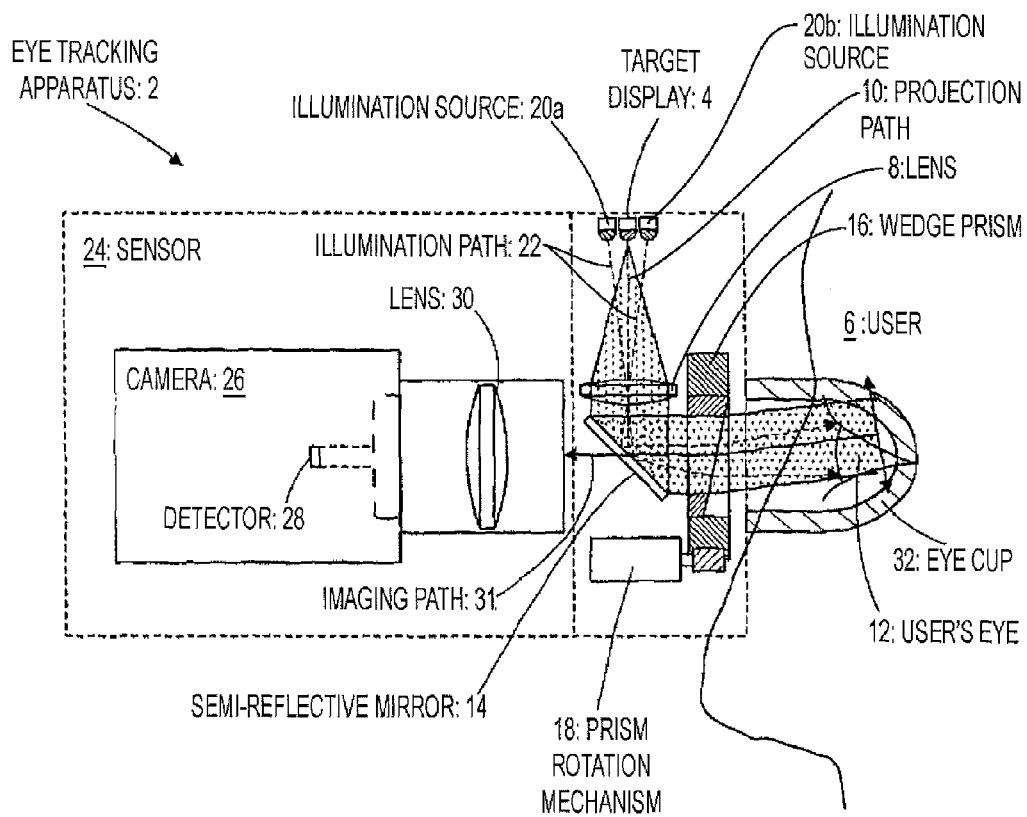
FIG. 1 shows a schematic cross-sectional view of an eye tracking apparatus according to one embodiment of the present invention incorporating a rotatable prism arranged to scan a target within a user's field of vision.

The eye tracking apparatus also comprises an illumination source comprising infrared light emitting diodes (IR LEDs) 20a, 20b arranged to illuminate the user's eye 12 along an illumination path 22 with electromagnetic radiation having a wavelength in the infrared spectrum. The lens 8 receives the infrared radiation emitted from the illumination source 20a, 20b and projects said infrared radiation along the illumination path 22 into the user's eye 12 via the semi-reflective mirror 14 and the wedge prism 16 that deviates the light by a small angle. An 8° wedge prism 16 has been used experimentally with good results.

Some of the infrared radiation illuminating the user's eye 12 produces a detectable bright reference point 23 thereon caused by specular reflection from the anterior surface of the user's eye 12. The illumination source is arranged at a distance from the user such that illuminating electromagnetic radiation emitted there from appears to be substantially collimated to the user. The illumination source is adapted, in use, to illuminate the user's eye and provide a spot corneal reflex as the reference point on the user's eye.

A sensor 24 comprising a camera 26 having a detector 28 and a lens 30 is also provided within the eye tracking apparatus 2 to image the user's eye 12. The camera 26 comprises a detector having a photosensitive device (PSD) for example a position sensing photodiode. Optionally, the detector 28 comprises a two-dimensional imaging array. The sensor 24 is configured to receive visible and infrared electromagnetic radiation reflected from the user's eye 12 along an imaging path 31 via the small angle wedge prism 16 and the semi-reflective mirror 14.

The eye tracking apparatus 2 also comprises an eye cup 32 arranged to shield the user's eye 12 from extraneous influences, to prohibit ambient light from interfering with the sensor 24 and to reduce unwanted movement between the eye tracking apparatus 2 and the user 6.

The method of operation of the eye tracking apparatus of FIG. 1 is now described by way of example only. The eye tracking apparatus is firstly arranged in optical communication with the user's eye 12, for example by positioning the eye cup 32 around the user's eye 12. The user's eye 12 is monitored by producing a target image from the target display 4 and projecting said target image into the user's eye 12 along a projection path 10 via the lens 8, the semi-reflective mirror 14 and the small angle wedge prism 16. At the same time, the user's eye 12 is illuminated with infrared radiation from illumination source 20a, 20b along an illumination path 22 via the lens 8, the semi-reflective mirror 14 and the wedge prism 16.

The wedge prism 16 is rotated by the prism rotation mechanism 18 at approximately 0.4 Hz about an axis which corresponds approximately to the user's line of sight in a 'straight ahead' position. The projection path 10 enters prism 16 coaxial with the rotation axis, thereby scanning the image of the target through an 8° radius circle in the user's field of vision. The reference point 23 (see FIG. 2) caused by reflection of infrared radiation from the anterior surface of the user's eye 12 also moves in synchronisation with projected target image due to the rotation of the wedge prism 16, by virtue of the common optical path through the prism 16.

The user's eye 12 tracks the distant target image as it moves through the 8° radius circle. The camera 26 is arranged to image the user's eye 12 along the same imaging path 31 as the target image is scanned in the user's field of vision. Since the imaging path 31 is also arranged along the common optical axis said imaging path passes through the wedge prism 16 and moves in synchronisation with the projected target image and the infrared illumination due to the rotation of the wedge prism 16.

The target display 4, the illumination source 20a, 20b and the sensor 24 are therefore arranged such that the projection path 10, the illumination path 22 and the imaging path all share a common path through the wedge prism 16 to the user's eye. Arranging the projection path 10, the illumination path 22 and the imaging path 31 along a common optical axis in this way ensures that, in use, the sensor 24 views the user's eye 12 along the target direction.

If the user's eye 12 tracks the target image perfectly then the user's eye 12 is directed along the imaging path 31 and the reference point 23 is centred on the user's eye throughout the 8° circular scan.

A direct determination of eye direction relative to the target and hence eye-target error is obtained by measuring a distance between reference point 23 on the user's eye and a physical feature of the user's eye 12, for example the centre or circumference of the pupil or iris of the user's eye 12.

Hence, an angular difference between the eye direction and the target direction is obtainable from the measured distance between the reference point 23 on the user's eye and the physical feature of the user's eye 12. Said angular difference is a quantitative assessment of how accurately the user's eye followed the image of the target as it was scanned through the user's field of vision.

The difference between the eye direction and target direction provides an eye tracking error assessment which may be subsequently used to assess the user's cognitive abilities, neurological deficiencies or cognitive impairment due to illness and/or brain injury.

The eye tracking apparatus is arranged to measure the distance between the reference point and the feature of the eye at a plurality of locations forming a locus of the target image scan. Eye direction relative to the target and hence eye-target error is therefore obtained at said plurality of locations. In an embodiment intended for medical diagnostic purposes, the measurements are made and stored at 250 Hz or more.

The accuracy of the eye tracking apparatus of FIG. 1 is principally governed by the accuracy with which the projection path 10, illumination path 22 and imaging path 31 are aligned along the common optical axis in the apparatus. In contrast, the accuracy of conventional eye tracking apparatuses is related to the accuracy of the calibration process. The present eye tracking apparatus and method therefore enable the angle between the target direction and the user's eye direction to be measured with high resolution (less than 0.05 degree r.m.s. noise) and high accuracy (less than 0.2 degree r.m.s. error).

Figure 2:
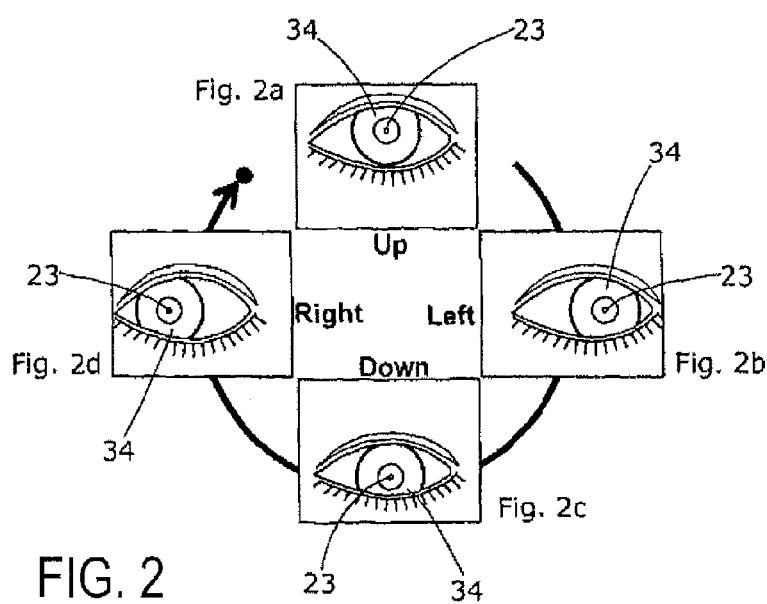
FIG. 2 shows a sequence of four images of a user's eye taken from an imaging sensor within the eye tracking apparatus of FIG. 1 while the user is looking at a target moving in a circular path around a central axis. Specifically.

FIG. 2 shows a sequence of four images of a user's eye 12 taken from the camera 26 within the eye tracking apparatus of FIG. 1 while the user 6 is looking at the moving image of the target from the display 4.

Specifically, FIG. 2a illustrates the position of the user's eye 12 when viewing the image of the target at the start of the scan. In FIG. 2a the target is arranged in a position above the scan centre. The reference point 23 is clearly seen as a bright reflection located substantially in the centre of the pupil 34 of the user's eye 12 indicating that the user is looking directly at the image of the target. FIG. 2b illustrates the position of the user's eye 12 when the target is arranged in a position to one side of the scan centre. Although eye 12 and the bright reference point 23 have both moved within the image, the reference point 23 remains in the centre of the pupil 34 of the user's eye 12 indicating that the user is still looking directly at the image of the target. In FIG. 2c the image of the target is arranged in a position below the scan centre. In FIG. 2c, the reference point 23 is once again concentric with the pupil 34 of the user's eye 12. Finally, FIG. 2d illustrates the position of the user's eye 12 when the image of the target is arranged in a position to the other side of the scan centre. The eye 12 and the reference point 23 have both moved within the image, but once again the reference point 23 remains in the centre of the pupil 34 of the user's eye 12 indicating that the user is still looking directly at the image of the target.

In the foregoing embodiments the infrared light emitting diodes (IR LEDs) 20a, 20b comprising the illumination source are located in close proximity to the target display 4 so as to produce a single reference point 23 on the user's eye 12. In this way and for the purposes of the embodiment of FIG. 1, the target and illumination source are effectively coincident. However, if the infrared light emitting diodes (IR LEDs) 20a, 20b are arranged in spaced relationship to target display 4 then a plurality of reference points 23 are formed by specular reflections from the anterior surface of the user's eye 12. For example, two infrared light emitting diodes (IR LEDs) 20a, 20b arranged in a spaced relationship would produce a pair of reflections; three light emitting diodes (IR LEDs) 20a, 20b arranged in a spaced relationship would produce a triad of reflections etc. The principle of operation of the eye tracking apparatus is the same as if a single reference point 23 is used, however in the case of a plurality of reflections a virtual reference point 23 may be employed which is, for example, equidistant from the actual reflections detectable on the user's eye.

In order to obtain coaxial alignment of the projection path 10 and the illumination path 22, the infrared light emitting diodes (IR LEDs) 20a, 20b and the display 4 are optionally arranged along the common optical axis using a beam splitter comprising one of a partially reflective mirror and a prism.

Figure 3:
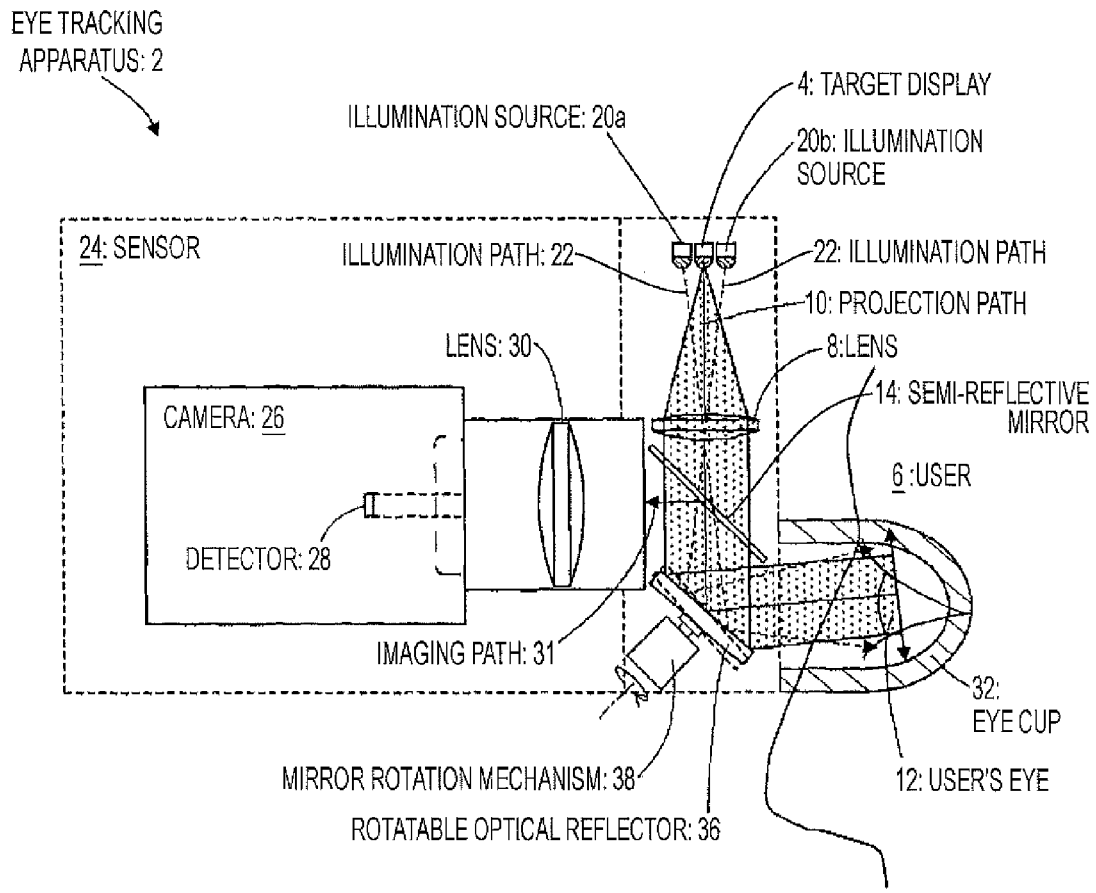
FIG. 3 shows a schematic cross-sectional view of an eye tracking apparatus according to a second embodiment of the present invention incorporating a rotatable reflector arranged to scan a target within a user's field of vision.

An alternative eye tracking apparatus is illustrated in FIG. 3 wherein like reference numerals identify corresponding or similar elements to those of the first embodiment shown in FIG. 1. The eye tracking apparatus of FIG. 3 is advantageous in allowing non-circular target motion and obviates a potential loss of image contrast which can occur with a wedge prism 16 due to back reflection of light there from.

In common with the embodiment of FIG. 1, the eye tracking apparatus of FIG. 3 comprises a target display 4 configured to project an image of a target along a projection path 10 into the field of vision of a user 6, an illumination source comprising infrared light emitting diodes (IR LEDs) 20a, 20b arranged to illuminate the user's eye 12 along an illumination path 22 with electromagnetic radiation having a wavelength in the infrared spectrum, and a sensor 24 comprising a camera 26 having a detector 28 and a lens 30 configured to receive visible and infrared electromagnetic radiation reflected from the user's eye 12 along an imaging path 31.

In the embodiment of FIG. 3, a lens 8 receives the visible electromagnetic radiation emitted from the target display 4 and the infrared electromagnetic radiation emitted by the IR LEDs 20a, 20b and projects said electromagnetic radiation into the user's eye via a semi-reflective mirror 14 and a rotatable optical reflector 36, for example a mirror. The reflector 36 has a reflective surface which is arranged at an angle of 4° to a plane normal to the shaft of a mirror rotation mechanism 38. In the case of a plane reflective mirror, the reflector 36 is canted at an angle of 4° off axis to a shaft of the mirror rotation mechanism 38.

In the eye tracking apparatus of FIG. 3, the sensor 24 is configured to receive visible and infrared electromagnetic radiation reflected from the user's eye 12 along an imaging path 31 via the rotatable reflector 36 and the semi-reflective mirror.

The eye cup 32 is retained in this embodiment to shield the user's eye 12 from extraneous influences, to prohibit ambient light from interfering with the sensor 24 and to reduce unwanted movement between the eye tracking apparatus 2 and the user 6.

In use, the rotatable reflector 36 is rotated on the shaft of the mirror rotation mechanism 38, at approximately 0.4 Hz. The projection path 10 is incident on the rotatable reflector 36, thereby scanning the image of the target through an 8° radius circle in the user's field of vision.

The user's eye 12 tracks the distant target image as it moves through the 8° radius circle. The camera 26 is arranged to image the user's eye 12 along the same imaging path 31 as the target image is scanned in the user's field of vision. Since the imaging path 31 is also arranged along the common optical axis said imaging path is reflected from the rotatable reflector 36 and moves in synchronisation with the projected target image and the infrared illumination due to the rotation of the reflector 36.

In common with the embodiment of FIG. 1, the target display 4, the illumination source 20a, 20b and the sensor 24 are arranged such that the projection path 10, the illumination path 22 and the imaging path 31 are all substantially coaxial on arrival at the moveable element, here reflector 36. Arranging the projection path 10, the illumination path 22 and the imaging path 31 along a common optical axis in this way ensures that, in use, the sensor 24 views the user's eye 12 along the target direction.

If the user's eye 12 tracks the target image perfectly then the user's eye 12 is directed along the imaging path 31 and the reference point 23 is centred on the user's eye throughout the 8° circular scan.

As before, a direct determination of eye direction relative to the target and hence eye-target error is obtained by measuring a distance between reference point 23 on the user's eye and a physical feature of the user's eye 12, for example the centre or circumference of the pupil or iris of the user's eye 12.

Hence, an angular difference between the eye direction and the target direction is obtainable from the measured distance between the reference point 23 on the user's eye and the physical feature of the user's eye 12. Said angular difference is a quantitative assessment of how accurately the user's eye followed the image of the target as it was scanned through the user's field of vision.

The difference between the eye direction and target direction provides an eye tracking error assessment which may be subsequently used to assess the user's cognitive abilities, neurological deficiencies or cognitive impairment due to illness and/or brain injury.

The output from the eye tracking apparatus 2 is output directly as a measure of the distance between the reference point and the feature of the eye or optionally as a measure of eye direction relative to the target. The output may be displayed directly or post processed as part of a medical apparatus.

Figure 4:
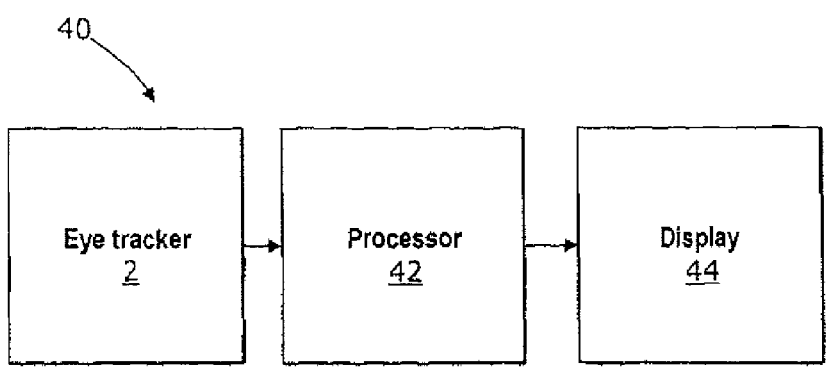
FIG. 4 shows schematic block diagram of a neurological monitoring apparatus having an eye tracking apparatus according to the present invention.

In particular, a medical apparatus 40 incorporating an eye tracking apparatus 2 according to the present invention is illustrated in FIG. 4. The medical apparatus 40 incorporates a processor adapted to interpret the eye measurements and to assess the cognitive state of the user. Results of the assessment are displayed on display 44 comprising a sophisticated display such as a video display or a rudimentary display such as a light emitting diode to indicate binary states (e.g. normal or impaired cognition).

In the foregoing embodiments the eye tracking apparatus is described as having a separate display 4 and illumination source comprising infrared light emitting diodes (IR LEDs) 20a, 20b arranged to illuminate the user's eye. However, in an alternative embodiment, the display 4 is arranged to project an image of the target and to illuminate the user's eye 12 using electromagnetic radiation in the visible waveband. In this embodiment, the IR LEDs 20a, 20b may be eliminated. Care must be taken in this embodiment not to dazzle the user 6 by using high intensity levels of illumination.

The eye tracking apparatus is arranged to measure the distance between the reference point and the feature of the eye at a plurality of locations forming a locus of the target image scan. Although the foregoing embodiments describe a step of scanning the image through a series of point forming a circle, other loci can be used. For example, the target image can be scanned along scan in the user's field of vision in at least one of a line, an arc, a circle, and an ellipse.

In these cases, a refractive or a reflective optical element is moved by at least one of a micro-electromechanical actuator, a motor, a piezo-micro-positioner, a galvanometer or any other suitable motive means to scan the projection axis, the illumination axis and the imaging axis within the user's field of vision.

As well as measuring smooth-pursuit eye tracking, the present eye tracking apparatus is configurable to move the target image in a discontinuous scan in order to assess a wider range of cognitive functions.

In another embodiment, the eye tracking apparatus comprises a modulator adapted to temporally vary at least one of the brightness and the hue of the image of the image of the target.

In view of the foregoing description it will be evident to a person skilled in the art that various modifications may be made within the scope of the invention.

Each feature disclosed in the description, and (where appropriate) the claims and drawings may be provided independently or in any appropriate combination.

In particular, with reference to the appended claims, features from dependent claims may be combined with those of the independent claims and features from respective independent claims may be combined in any appropriate manner and not merely in the specific combinations enumerated in the claims.

The invention claimed is:

1. An eye tracking apparatus comprising
a) a target display adapted to project a moveable image of a target into a user's field of vision,
b) an illumination source adapted to project a reference point onto a user's eye,
c) a sensor arranged to monitor a user's eye, including the reference point reflected from the eye, and
d) a processor adapted to receive information from the sensor, and to determine the position of a feature of a user's eye relative to the reference point,
wherein the apparatus is arranged such that said determined position provides a direct indication of eye direction relative to the target direction.

2. An eye tracking apparatus according to claim 1, the target display being adapted to project the moveable image along a projection path, the illumination source being adapted to project a reference point along an illumination path, the sensor being adapted to monitor the user's eye along an imaging path, and wherein at least a portion of the projection path, the illumination path and the imaging path are arranged to be substantially coaxial.

3. An eye tracking apparatus according to claim 1 adapted to scan the illumination path, the projection path and the imaging path in synchronisation within the user's field of vision.

4. An eye tracking apparatus according to claim 1 wherein the processor is adapted to determining a distance between the position of the reference point and the physical feature of the user's eye.

5. An eye tracking apparatus according to claim 4 wherein the processor is adapted to convert the determined distance into a measurement of an angle between the target direction and the user's eye direction.

6. An eye tracking apparatus according to claim 1 wherein feature of the user's eye comprises at least one of the user's pupil and the user's iris.

7. An eye tracking apparatus according to claim 1 adapted to scan the image of the target in the user's field of vision with a substantially constant angular velocity.

8. An eye tracking apparatus according to claim 1 adapted to scan the image of the target in the user's field of vision with a varying angular velocity.

9. An eye tracking apparatus according to claim 1 adapted to scan the image of the target in the user's field of vision along a controlled path that includes at least one of a point, a line, an arc, a circle, and an ellipse.

10. An eye tracking apparatus according to claim 1 comprising a modulator adapted to temporally vary at least one of the brightness, the hue, the shape and the form of the image of the target.

11. A method of eye monitoring, in which a moveable image of a target is projected into a user's field of vision, and an image of the user's eye is formed on an image sensor, said method comprising:
  (a) projecting a reference point onto the user's eye,
  (b) arranging for the selected reference point to provide, in the image, an indication of the position of the target on the user's eye,
  (c) analysing the image to determine the position of a feature of the user's eye with respect to the reference point.

12. A method of eye monitoring according to claim 11 comprising projecting the moveable target and the reference point along a common projection path and monitoring the user's eye along an imaging path, wherein at least a portion of said imaging path is substantially coaxial with said common projection path.

13. A method of eye monitoring according to claim 11 comprising the step of scanning the common projection path and the imaging path in synchronisation within the user's field of vision.

14. A method of eye monitoring according to claim 11 comprising the step of analysing the image to determine a distance between the feature of the user's eye and the position of the reference point.

15. A method of eye monitoring according to claim 14 comprising the further step of converting the determined distance into a measurement of an angle between the target direction and the user's eye direction.

16. A method of eye monitoring according to claim 11 wherein the feature of the user's eye comprises at least one of the user's pupil and the user's iris.

17. A method of eye monitoring according to claim 11 comprising the step of scanning the image of the target in the user's field of vision with a substantially constant angular velocity.

18. A method of eye monitoring according to claim 11 comprising the step of scanning the image of the target in the user's field of vision with a varying angular velocity.

19. A method of eye tracking according to claim 11 comprising scanning the image of the target in the user's field of vision along a controlled path that includes at least one of a point, a line, an arc, a circle, and an ellipse.

20. A method of eye tracking according to claim 11 comprising the step of temporally varying at least one of the brightness, the hue, the shape and the form of the image of the target.

21. An eye tracking apparatus comprising
  a) a target display adapted to project a moveable image of a target into a user's field of vision,
  b) an illumination source adapted to project a reference point onto a user's eye,
  c) a sensor arranged to monitor a user's eye, including the reference point reflected from the eye, and
  d) a processor adapted to receive information from the sensor, and to determine therefrom the position of a feature of a user's eye relative to the reference point,
  wherein the apparatus is arranged such that the determined position provides a direct indication of eye direction relative to the target direction,
  the target display is adapted to project the moveable image along a projection path,
  the illumination source is adapted to project the reference point along an illumination path, and
  the projection path and the illumination path are synchronized.

* * * * *